(12) United States Patent
Juan

(10) Patent No.: US 7,640,049 B2
(45) Date of Patent: *Dec. 29, 2009

(54) PHYSIOLOGICAL MEASUREMENT STRIP WITH DISPLAY

(76) Inventor: Cheng-Pin Juan, 235 Chung-Ho, Box 8-24, Taipei (TW)

( * ) Notice: Subject to any disclaimer, the term of this patent is extended or adjusted under 35 U.S.C. 154(b) by 347 days.

This patent is subject to a terminal disclaimer.

(21) Appl. No.: 11/522,809

(22) Filed: Sep. 18, 2006

(65) Prior Publication Data

US 2008/0082010 A1     Apr. 3, 2008

(51) Int. Cl.
*A61B 5/04* (2006.01)
*A61B 5/02* (2006.01)

(52) U.S. Cl. .................. 600/390; 600/502; 600/523

(58) Field of Classification Search .......... 600/386, 600/390, 502, 523
See application file for complete search history.

(56) References Cited

U.S. PATENT DOCUMENTS

| | | | | |
|---|---|---|---|---|
| 3,802,698 A | * | 4/1974 | Burian et al. | 600/520 |
| 3,978,849 A | * | 9/1976 | Geneen | 600/503 |
| 4,129,125 A | * | 12/1978 | Lester et al. | 600/484 |
| 5,003,984 A | * | 4/1991 | Muraki et al. | 600/523 |
| 5,778,880 A | * | 7/1998 | Chen | 600/509 |
| 6,530,886 B1 | * | 3/2003 | Ishida et al. | 600/442 |
| 6,561,987 B2 | * | 5/2003 | Pail | 600/534 |
| 7,428,433 B2 | * | 9/2008 | Juan | 600/390 |

\* cited by examiner

*Primary Examiner*—Lee S Cohen

(57) ABSTRACT

A physiological measurement strip with a display comprises a strip and an electronic device. A surface of at least one end of the strip has a conductive portion; the conductive portion is connected to the electronic device; the electronic device is installed with a processor; an outer side of the electronic device has a display, thus the processor can measure physiological data through the conductive portion and the data is displayed on the display. The electronic device has a speaker, alarm lamps and a level meter and can transfer data wirelessly. The alarm lamps include a red light, a yellow light and a green light. Two ends of the electronic device have buckling grooves, respectively; and two ends of the strip have buckles, respectively, the buckles and buckling groove are conductive. The electronic device is installed with an auxiliary conduction portion.

1 Claim, 5 Drawing Sheets

US 7,640,049 B2

PHYSIOLOGICAL MEASUREMENT STRIP WITH DISPLAY

FIELD OF THE INVENTION

The present invention relates to physiological measurement devices, and particularly to a physiological measurement strip with a display, which can display the physiological data real time and present the physiological conditions by alarm lamps and speaker.

BACKGROUND OF THE INVENTION

For the patients of serious diseases, they must wear physiological measurement strips for measuring physiological data real time and providing alert message to users or doctors so as to trace the body condition of the patient.

In the present invention, the physiological measurement strip has an elastic strip and a measurement unit. The measurement unit has a body and a signal processor. The body is made of flexible material. The backside of the body has two conductive cloth. The processor is installed at a front side of the body and is conductive to the conductive cloth. Two ends of the elastic strip are buckled to the body so that it can be worn on the breast of the user for measuring the physiological data of human body. The data are transferred to a computer, a PDA, a handset, etc. Thereby the patients and medical persons can know the conditions of the body.

However, the prior art physiological measurement strip is not an ideal one. This prior art strip only has an LED light to indicate whether the user's body is normal. No display is quipped. Thus, various receivers are used for providing real time data to users. Furthermore the physiological measurement strip cannot provide other auxiliary functions, such as emergency conditions, to users. Thereby the prior art physiological measurement strip is not a practical one and is needed to be improved.

SUMMARY OF THE INVENTION

Accordingly, the primary object of the present invention is to provide a physiological measurement display which can display the physiological data real time and present the physiological conditions by alarm lamps and speaker.

To achieve above objects, the present invention provides a physiological measurement strip with a display which comprises a strip and an electronic device. A surface of at least one end of the strip has a conductive portion; the conductive portion is connected to the electronic device; the electronic device is installed with a processor; an outer side of the electronic device has a display, thus the processor can measure physiological data through the conductive portion and the data is displayed on the display.

The electronic device has a speaker, alarm lamps and a level meter. The electronic device can transfer data wirelessly. The alarm lamps include a red light, a yellow light and a green light. Two ends of the electronic device have buckling grooves, respectively; and two ends of the strip have buckles, respectively, the buckles and buckling groove are conductive; in assembly, the buckles are buckled to the buckling grooves. The electronic device is installed with an auxiliary conduction portion and the auxiliary conduction portion with the conductive portion can measure data so as to increase the accuracy in measurement.

The various objects and advantages of the present invention will be more readily understood from the following detailed description when read in conjunction with the appended drawing.

DETAILED DESCRIPTION OF THE INVENTION

Figure 1:
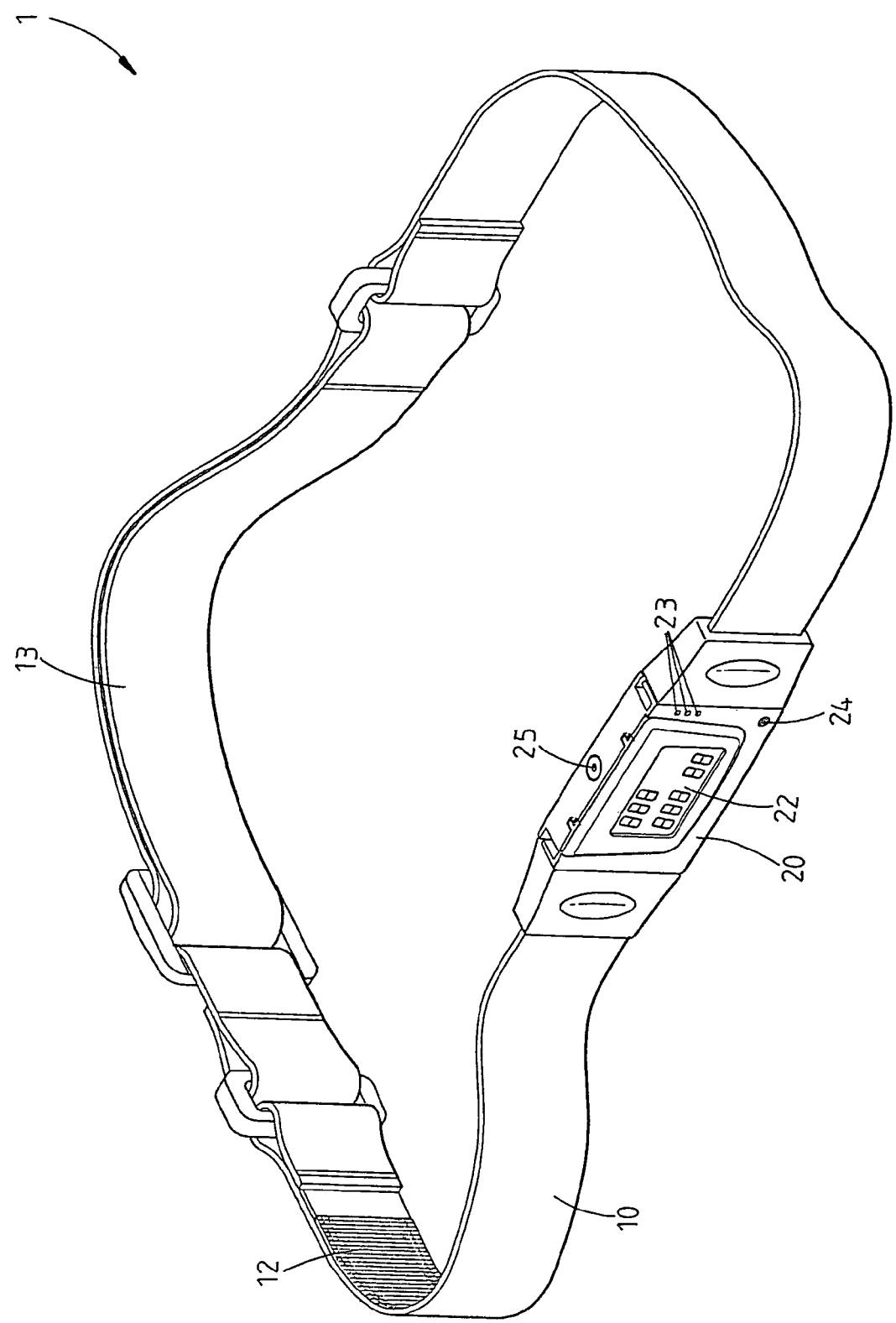
FIG. 1 is a perspective view of the physiological measurement strip with a display of the present invention.

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

Referring to FIGS. 1 to 4, the physiological measurement strip with a display of the present invention is illustrated. The present invention has the following elements.

A strip 10 is two buckles 11 at two ends thereof. The buckles 11 are conductive. An inner side of the strip 10 is a conductive portion 12 made of conductive material. The conductive portion 12 may have a form of a web, a stripe or a sheet. In use, the conductive portion 12 is in contact to a body of the user so that an electronic device 20 can perform physiological measurement. The strip 10 has an adjustable section 13 for adjusting a length of the strip 10.

The electronic device 20 has two ends. Each end of the electronic device 20 has a buckling groove 21 corresponding to the buckle 11. An inner side of the buckling groove 21 is conductive for electrically connecting the buckle 11 of the strip 10. The electronic device 20 has a processor therein (not shown). Thereby the electronic device 20 can measure the physiological data through the conductive portion 12. A display 22 is installed at an outer side of the electronic device 20. One end of the display 22 is pivotally connected to the electronic device 20. The display 22 serves to display the measure data of the electronic device 20. The display 22 is turnable for viewing data. The electronic device 20 is installed with alarm lamps 23 of different colors and speaker 24 as auxiliary device for indication. The alarm lamps 23 include for example, a red alarm lamp, a yellow alarm lamp and a green alarm lamp for indication different levels. The electronic device 20 is installed with a level meter 25 which has a form of buoyage for showing whether an object is horizontal and shows the shift from horizontality so as to help the patient with low sense of equilibrium from fall down.

Figure 2:
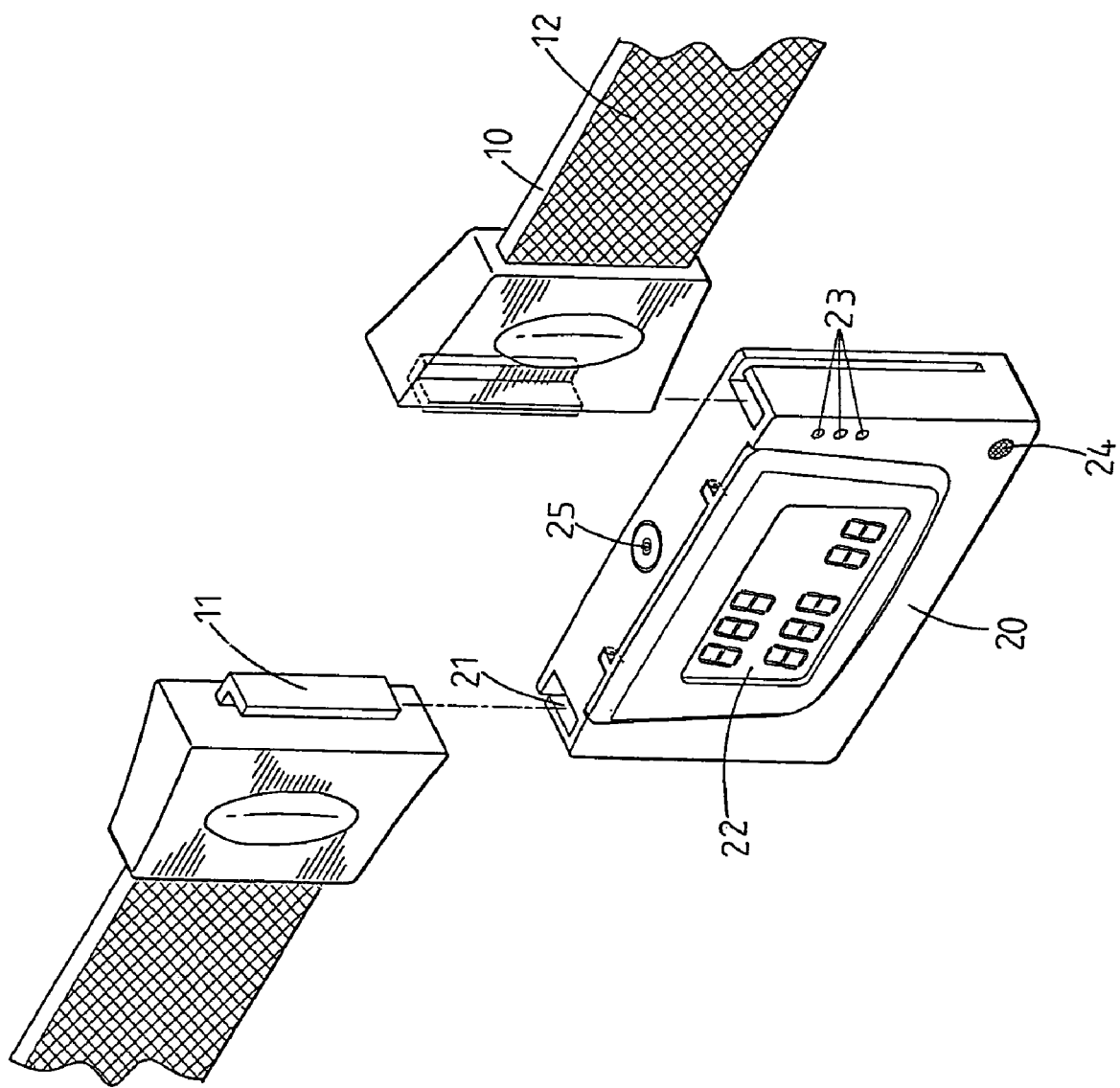
FIG. 2 is an assembled schematic view of the physiological measurement strip with a display of the present invention.

In use of the present invention, the strip 10 is adjusted to a proper length by adjusting the adjustable section 13. Referring to FIG. 2, the buckles 11 of the strip 10 are buckled to the buckling grooves 21 of the electronic device 20. The conductive portion 12 of the strip 10 is conductive to the electronic device 20. The conductive portion 12 is adhered to the body of the user. The processor in the electronic device 20 will measure the physiological data of the user, such as pulses, body temperature, etc. Other than wireless function, the electronic device 20 can provide the physiological data to the user through the display 22, alarm lamps 23, speaker 24 and level meter 25.

Figure 3:
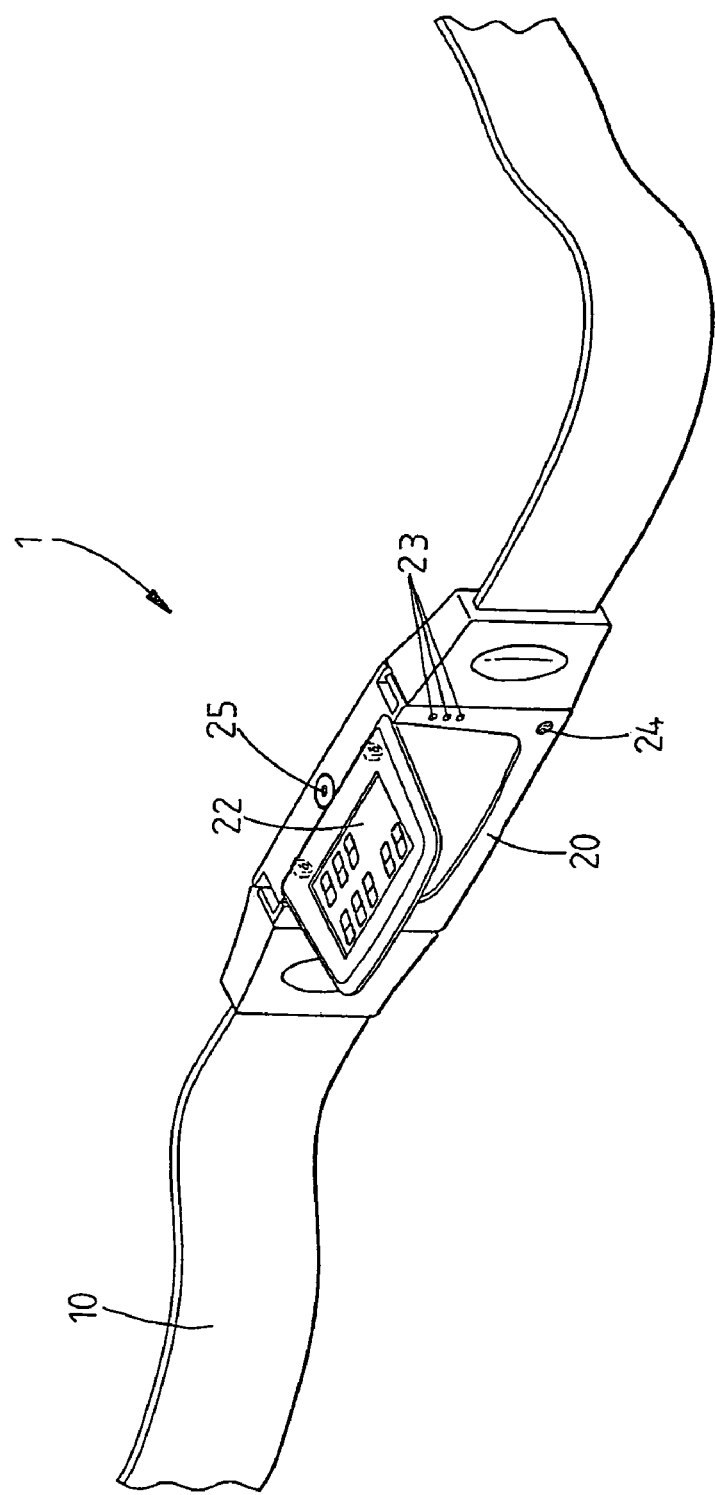
FIG. 3 is a schematic view showing the turning operation of the display of the present invention.
Figure 4:
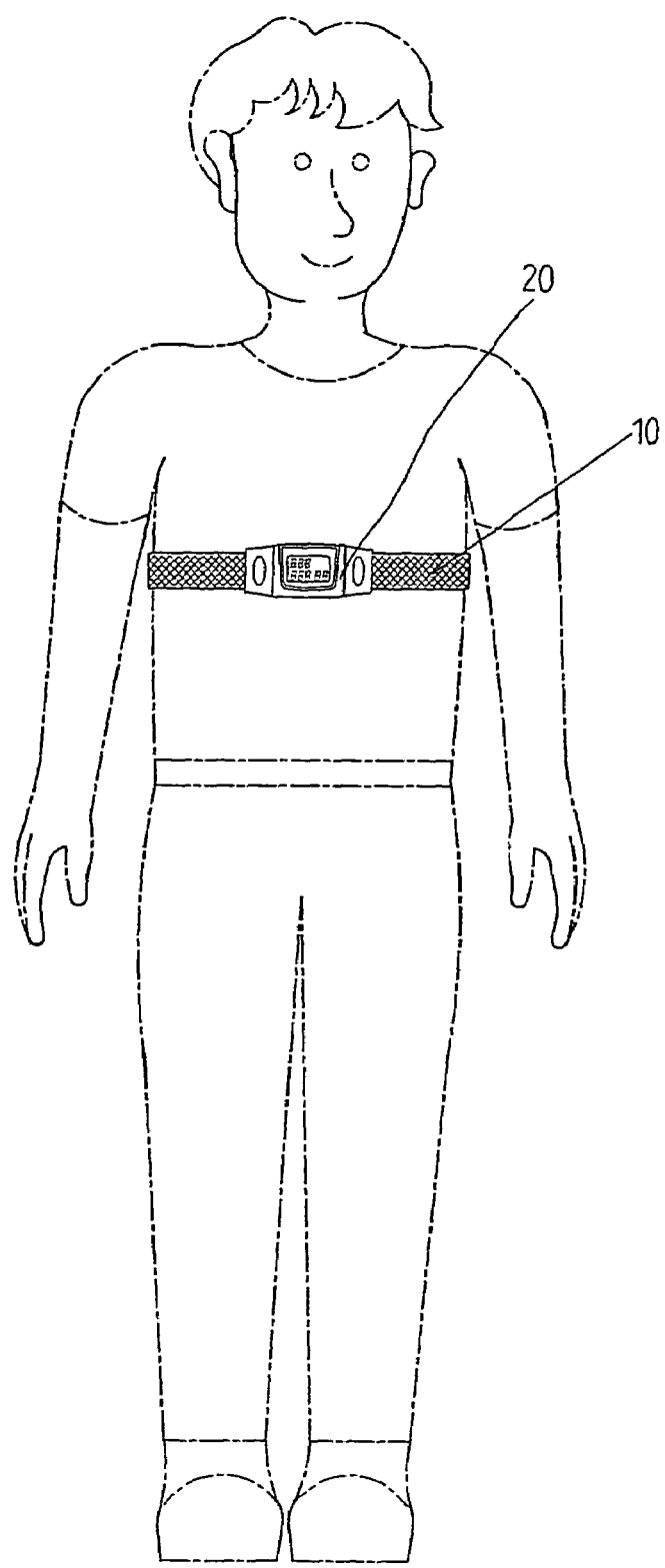
FIG. 4 is a schematic view showing the use of the physiological measurement strip with a display of the present invention.

Referring to FIG. 3, the display 22 can be turned upwards to a predetermined angle so that user can view the data on the display 22 easily.

Moreover, the electronic device 20 has auxiliary devices, such as alarms or speaker 24. The alarm lamps 23 can present different colors. When the physiological data of the user is normal, the green light lights up. If the physiological data of the user is not so good, the yellow light lights up. If the physiological data presents that the body of the user is bad, the red light lights up. The speaker 24 emits sounds to match the condition of the physiological data so that the user can understand the body condition thereof.

The level meter 25 has the effect of helping the user with bad sense of equilibrium. The level meter 25 is a sealing space filled with liquid. The space has an indication material the density of which is smaller than the liquid. The indication will shift with the horizontality and direction of the user so that the user can understand the equilibrium thereof to prevent from falling down.

Figure 5:
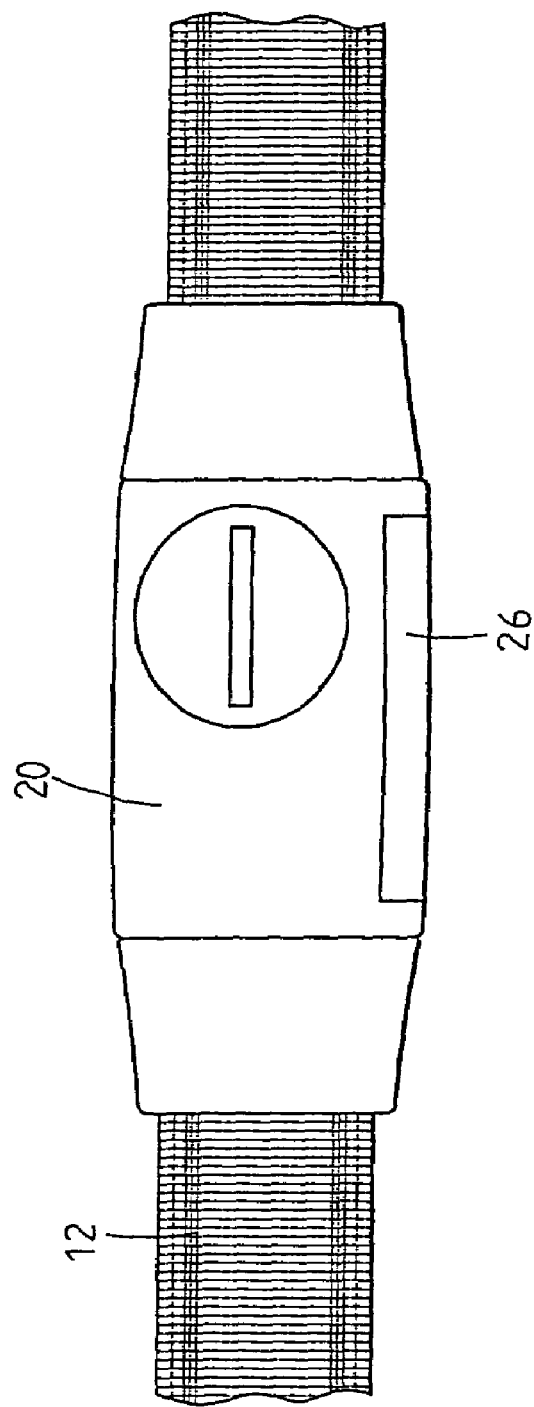
FIG. 5 is a schematic perspective view about the second embodiment of the physiological measurement strip with a display of the present invention.

Referring to FIG. 5, the second embodiment of the present invention is illustrated. In this embodiment, those identical to the above mentioned embodiment will not be further described herein. Only those difference are disclosed.

An auxiliary conduction portion 26 is installed on a surface of the electronic device 20 which can contact the user. The auxiliary conduction portion 26 with the conductive portion 12 can measure data with waveform by measuring three points so as to increase the accuracy in measurement.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A physiological measurement strip with a display comprising:
   a strip, the strip having an adjustable section for adjusting a length thereof, the strip having two buckles respectively disposed on two ends thereof, the strip having a conductive portion disposed on a surface of at least one end thereof; and
   an electronic device electronically connected to the strip, the electronic device having a speaker disposed thereon for emitting sounds, the electronic device having level meter disposed thereon for showing a horizontality thereof, the electronic device having multiple alarm lamps disposed thereon, the multiple lamps including a red light, a yellow light, and a green light, the electronic device having two buckling grooves respectively disposed on two ends thereof for conductively connecting to the buckles of the strip, the electronic device having a processor installed therein, the electronic device having an auxiliary conduction portion installed thereon, the electronic device having a display pivotally installed on an outer side thereof for adjusting a viewing angle;
   wherein the conductive portion is connected to the electronic device; the buckling grooves and the buckles are conductive such that the buckles are buckled to the bucking grooves in assembly; the auxiliary conduction portion with the conductive portion can measure data so as to increase the accuracy in measurement; the processor can measure physiological data through the conductive portion and the data is displayed on the display; the electronic device transfers data wirelessly.

* * * * *